(12) United States Patent
Kugler et al.

(10) Patent No.: US 8,636,712 B2
(45) Date of Patent: Jan. 28, 2014

(54) ENDOVASCULAR DEVICES AND METHODS

(75) Inventors: Chad J. Kugler, Andover, MN (US);
Robert E. Atkinson, White Bear Lake, MN (US)

(73) Assignee: Bridgepoint Medical, Inc., Plymouth, MN (US)

( * ) Notice: Subject to any disclaimer, the term of this patent is extended or adjusted under 35 U.S.C. 154(b) by 63 days.

(21) Appl. No.: 13/214,141

(22) Filed: Aug. 19, 2011

(65) Prior Publication Data
US 2012/0071854 A1 Mar. 22, 2012

Related U.S. Application Data

(63) Continuation of application No. 11/518,431, filed on Sep. 11, 2006, now Pat. No. 8,025,655.

(60) Provisional application No. 60/716,287, filed on Sep. 12, 2005, provisional application No. 60/717,726, filed on Sep. 15, 2005.

(51) Int. Cl.
A61M 31/00 (2006.01)

(52) U.S. Cl.
USPC .......................................................... 604/509

(58) Field of Classification Search
USPC ..................... 606/167; 604/500, 507–510, 22
See application file for complete search history.

(56) References Cited

U.S. PATENT DOCUMENTS

| | | | |
|---|---|---|---|
| 4,020,829 A | 5/1977 | Willson et al. | |
| 4,233,983 A | 11/1980 | Rocco | |
| 4,569,347 A | 2/1986 | Frisbie | |
| 4,581,017 A | 4/1986 | Sahota | |
| 4,621,636 A | 11/1986 | Fogarty | |
| 4,747,821 A | 5/1988 | Kensey et al. | |
| 4,762,130 A | 8/1988 | Fogarty et al. | |
| 4,774,949 A | 10/1988 | Fogarty | |
| 4,819,634 A | 4/1989 | Shiber | |
| 4,878,495 A | 11/1989 | Grayzel | |
| 4,976,689 A | 12/1990 | Buchbinder et al. | |
| 4,979,939 A | 12/1990 | Shiber | |

(Continued)

FOREIGN PATENT DOCUMENTS

| | | | |
|---|---|---|---|
| WO | WO 0178822 A2 | 10/2001 | |
| WO | WO 2007/033052 A2 | 3/2007 | |

(Continued)

OTHER PUBLICATIONS

Bolia, Amman, Subintimal Angioplasty: *Which Cases to Choose, How to Avoid Pitfalls and Technical Tips*, Combined Session: Vascular Surgery and Interventional Radiology, pp. III 8.1-8.3.

(Continued)

*Primary Examiner* — Bhisma Mehta
*Assistant Examiner* — Bradley Osinski
(74) *Attorney, Agent, or Firm* — Seager, Tufte & Wickhem, LLC

(57) ABSTRACT

Devices and methods for the treatment of chronic total occlusions are provided. One disclosed embodiment comprises a method of facilitating treatment via a vascular wall defining a vascular lumen containing an occlusion therein. The method includes providing an intravascular device having a distal portion, inserting the device into the vascular lumen, positioning the distal portion in the vascular wall to at least partially surround the occlusion, and removing at least a portion of the surrounded occlusion from the lumen.

4 Claims, 13 Drawing Sheets

(56) References Cited

U.S. PATENT DOCUMENTS

| | | | |
|---|---|---|---|
| 4,990,134 | A | 2/1991 | Auth |
| 5,071,406 | A | 12/1991 | Jang |
| 5,127,917 | A | 7/1992 | Niederhauser et al. |
| 5,193,546 | A | 3/1993 | Shaknovich |
| 5,201,753 | A | 4/1993 | Lampropoulos et al. |
| 5,263,493 | A | 11/1993 | Avitall |
| 5,275,610 | A | 1/1994 | Eberbach |
| 5,324,263 | A | 6/1994 | Kraus et al. |
| 5,356,418 | A | 10/1994 | Shturman |
| 5,372,587 | A | 12/1994 | Hammerslag et al. |
| 5,383,856 | A | 1/1995 | Bersin |
| 5,385,152 | A | 1/1995 | Abele et al. |
| 5,409,453 | A | 4/1995 | Lundquist et al. |
| 5,415,637 | A | 5/1995 | Khosravi |
| 5,464,395 | A | 11/1995 | Faxon et al. |
| 5,501,667 | A | 3/1996 | Verduin, Jr. |
| 5,505,702 | A | 4/1996 | Arney |
| 5,534,007 | A | 7/1996 | St. Germain et al. |
| 5,555,883 | A | 9/1996 | Avitall |
| 5,571,122 | A | 11/1996 | Kelly et al. |
| 5,571,169 | A | 11/1996 | Plaia et al. |
| 5,603,720 | A | 2/1997 | Kieturakis |
| 5,643,298 | A | 7/1997 | Nordgren et al. |
| 5,645,529 | A | 7/1997 | Fagan et al. |
| 5,655,548 | A | 8/1997 | Nelson et al. |
| 5,695,506 | A | 12/1997 | Pike et al. |
| 5,728,133 | A | 3/1998 | Kontos |
| 5,741,270 | A | 4/1998 | Hansen et al. |
| 5,741,429 | A | 4/1998 | Donadio, III et al. |
| 5,779,721 | A | 7/1998 | Nash |
| 5,807,241 | A | 9/1998 | Heimberger |
| 5,824,071 | A | 10/1998 | Nelson et al. |
| 5,830,222 | A | 11/1998 | Makower |
| 5,830,224 | A | 11/1998 | Cohn et al. |
| 5,843,050 | A | 12/1998 | Jones et al. |
| 5,882,329 | A | 3/1999 | Patterson et al. |
| 5,910,133 | A | 6/1999 | Gould et al. |
| 5,916,194 | A | 6/1999 | Jacobsen et al. |
| 5,935,108 | A | 8/1999 | Katoh et al. |
| 5,944,686 | A | 8/1999 | Patterson et al. |
| 5,954,713 | A | 9/1999 | Newman et al. |
| 5,957,900 | A | 9/1999 | Ouchi |
| 5,968,064 | A | 10/1999 | Selmon et al. |
| 5,989,276 | A | 11/1999 | Houser et al. |
| 6,010,449 | A | 1/2000 | Selmon et al. |
| 6,013,055 | A | 1/2000 | Bampos et al. |
| 6,015,405 | A | 1/2000 | Schwartz et al. |
| 6,022,343 | A | 2/2000 | Johnson et al. |
| 6,036,707 | A | 3/2000 | Spaulding |
| 6,036,717 | A | 3/2000 | Mers Kelly et al. |
| 6,059,750 | A | 5/2000 | Fogarty et al. |
| 6,068,638 | A | 5/2000 | Makower |
| 6,071,281 | A | 6/2000 | Burnside et al. |
| 6,071,292 | A | 6/2000 | Makower et al. |
| 6,081,738 | A | 6/2000 | Hinohara et al. |
| 6,099,542 | A | 8/2000 | Cohn et al. |
| 6,117,064 | A | 9/2000 | Apple et al. |
| 6,120,516 | A | 9/2000 | Selmon et al. |
| 6,126,649 | A | 10/2000 | VanTassel et al. |
| 6,155,264 | A | 12/2000 | Ressemann et al. |
| 6,157,852 | A | 12/2000 | Selmon et al. |
| 6,159,225 | A | 12/2000 | Makower |
| 6,183,432 | B1 | 2/2001 | Milo |
| 6,186,972 | B1 | 2/2001 | Nelson et al. |
| 6,190,353 | B1 | 2/2001 | Makower et al. |
| 6,203,559 | B1 | 3/2001 | Davis et al. |
| 6,217,527 | B1 | 4/2001 | Selmon et al. |
| 6,217,549 | B1 | 4/2001 | Selmon et al. |
| 6,221,049 | B1 | 4/2001 | Selmon et al. |
| 6,231,546 | B1 | 5/2001 | Milo et al. |
| 6,231,587 | B1 | 5/2001 | Makower |
| 6,235,000 | B1 | 5/2001 | Milo et al. |
| 6,241,667 | B1 | 6/2001 | Vetter et al. |
| 6,246,914 | B1 | 6/2001 | de la Rama et al. |
| 6,254,588 | B1 | 7/2001 | Jones et al. |
| 6,258,052 | B1 | 7/2001 | Milo |
| 6,266,550 | B1 | 7/2001 | Selmon et al. |
| 6,277,133 | B1 | 8/2001 | Kanesaka |
| 6,283,940 | B1 | 9/2001 | Mulholland |
| 6,283,951 | B1 | 9/2001 | Flaherty et al. |
| 6,283,983 | B1 | 9/2001 | Makower et al. |
| 6,287,317 | B1 | 9/2001 | Makower et al. |
| 6,302,875 | B1 | 10/2001 | Makower et al. |
| 6,330,884 | B1 | 12/2001 | Kim |
| 6,337,142 | B2 | 1/2002 | Harder et al. |
| 6,358,244 | B1 | 3/2002 | Newman et al. |
| 6,375,615 | B1 | 4/2002 | Flaherty et al. |
| 6,379,319 | B1 | 4/2002 | Garibotto et al. |
| 6,387,119 | B2 | 5/2002 | Wolf et al. |
| 6,398,798 | B2 | 6/2002 | Selmon et al. |
| 6,416,523 | B1 | 7/2002 | Lafontaine |
| 6,428,552 | B1 | 8/2002 | Sparks |
| 6,432,127 | B1 | 8/2002 | Kim et al. |
| 6,447,539 | B1 | 9/2002 | Nelson et al. |
| 6,475,226 | B1 * | 11/2002 | Belef et al. .................. 606/185 |
| 6,485,458 | B1 | 11/2002 | Takahashi |
| 6,491,660 | B2 | 12/2002 | Guo et al. |
| 6,491,707 | B2 | 12/2002 | Makower et al. |
| 6,506,178 | B1 | 1/2003 | Schubart et al. |
| 6,508,824 | B1 | 1/2003 | Flaherty et al. |
| 6,508,825 | B1 | 1/2003 | Selmon et al. |
| 6,511,458 | B2 | 1/2003 | Milo et al. |
| 6,514,217 | B1 | 2/2003 | Selmon et al. |
| 6,544,230 | B1 | 4/2003 | Flaherty et al. |
| 6,561,998 | B1 | 5/2003 | Roth et al. |
| 6,565,583 | B1 | 5/2003 | Deaton et al. |
| 6,569,143 | B2 | 5/2003 | Alchas et al. |
| 6,569,145 | B1 | 5/2003 | Shmulewitz et al. |
| 6,569,150 | B2 | 5/2003 | Teague et al. |
| 6,579,311 | B1 | 6/2003 | Makower |
| 6,589,164 | B1 | 7/2003 | Flaherty |
| 6,599,304 | B1 | 7/2003 | Selmon et al. |
| 6,602,241 | B2 | 8/2003 | Makower et al. |
| 6,613,081 | B2 | 9/2003 | Kim et al. |
| 6,616,675 | B1 | 9/2003 | Evard et al. |
| 6,623,448 | B2 | 9/2003 | Slater |
| 6,638,247 | B1 | 10/2003 | Selmon et al. |
| 6,638,293 | B1 | 10/2003 | Makower et al. |
| 6,655,386 | B1 | 12/2003 | Makower et al. |
| 6,656,195 | B2 | 12/2003 | Peters et al. |
| 6,660,024 | B1 | 12/2003 | Flaherty et al. |
| 6,669,709 | B1 | 12/2003 | Cohn et al. |
| 6,685,648 | B2 | 2/2004 | Flaherty et al. |
| 6,685,716 | B1 | 2/2004 | Flaherty et al. |
| 6,694,983 | B2 | 2/2004 | Wolf et al. |
| 6,709,444 | B1 | 3/2004 | Makower |
| 6,719,725 | B1 | 4/2004 | Milo et al. |
| 6,726,677 | B1 | 4/2004 | Flaherty et al. |
| 6,746,426 | B1 | 6/2004 | Flaherty et al. |
| 6,746,462 | B1 | 6/2004 | Selmon et al. |
| 6,746,464 | B1 | 6/2004 | Makower |
| 6,786,884 | B1 | 9/2004 | DeCant, Jr. et al. |
| 6,800,085 | B2 | 10/2004 | Selmon et al. |
| 6,824,550 | B1 | 11/2004 | Noriega et al. |
| 6,830,577 | B2 | 12/2004 | Nash et al. |
| 6,837,868 | B1 | 1/2005 | Fajnztajn |
| 6,860,892 | B1 | 3/2005 | Tanaka et al. |
| 6,863,684 | B2 | 3/2005 | Kim et al. |
| 6,866,676 | B2 | 3/2005 | Kieturakis et al. |
| 6,884,225 | B2 | 4/2005 | Kato et al. |
| 6,905,505 | B2 | 6/2005 | Nash et al. |
| 6,929,009 | B2 | 8/2005 | Makower et al. |
| 6,936,056 | B2 | 8/2005 | Nash et al. |
| 6,942,641 | B2 | 9/2005 | Seddon |
| 6,949,125 | B2 | 9/2005 | Robertson |
| 6,991,617 | B2 | 1/2006 | Hektner et al. |
| 7,004,173 | B2 | 2/2006 | Sparks et al. |
| 7,056,325 | B1 | 6/2006 | Makower et al. |
| 7,059,330 | B1 | 6/2006 | Makower et al. |
| 7,083,588 | B1 | 8/2006 | Shmulewitz et al. |
| 7,094,230 | B2 | 8/2006 | Flaherty et al. |
| 7,105,031 | B2 | 9/2006 | Letort |
| 7,134,438 | B2 | 11/2006 | Makower et al. |
| 7,137,990 | B2 | 11/2006 | Hebert et al. |

(56) References Cited

U.S. PATENT DOCUMENTS

| | | | |
|---|---|---|---|
| 7,159,592 B1 | 1/2007 | Makower et al. |
| 7,179,270 B2 | 2/2007 | Makower |
| 7,191,015 B2 | 3/2007 | Lamson et al. |
| 7,229,421 B2 | 6/2007 | Jen et al. |
| 7,316,655 B2 | 1/2008 | Garibotto et al. |
| 7,377,910 B2 | 5/2008 | Katoh et al. |
| 7,465,286 B2 | 12/2008 | Patterson et al. |
| 2001/0000041 A1 | 3/2001 | Selmon et al. |
| 2001/0056273 A1 | 12/2001 | C |
| 2002/0029052 A1 | 3/2002 | Evans et al. |
| 2002/0052637 A1 | 5/2002 | Houser et al. |
| 2002/0103459 A1 | 8/2002 | Sparks et al. |
| 2003/0028200 A1 | 2/2003 | Berg et al. |
| 2003/0040737 A1 | 2/2003 | Merril et al. |
| 2003/0109809 A1 | 6/2003 | Jen et al. |
| 2003/0120195 A1* | 6/2003 | Milo et al. ............... 604/19 |
| 2003/0167038 A1 | 9/2003 | Yozu et al. |
| 2003/0236542 A1 | 12/2003 | Makower |
| 2004/0015193 A1 | 1/2004 | Lamson et al. |
| 2004/0059280 A1 | 3/2004 | Makower et al. |
| 2004/0102719 A1 | 5/2004 | Keith et al. |
| 2004/0133225 A1 | 7/2004 | Makower |
| 2004/0158143 A1 | 8/2004 | Flaherty et al. |
| 2004/0167554 A1* | 8/2004 | Simpson et al. ............ 606/159 |
| 2004/0230156 A1 | 11/2004 | Schreck et al. |
| 2004/0249277 A1 | 12/2004 | Kato et al. |
| 2004/0249338 A1 | 12/2004 | DeCant, Jr. et al. |
| 2005/0038467 A1 | 2/2005 | Hebert et al. |
| 2005/0049574 A1 | 3/2005 | Petrick et al. |
| 2005/0171478 A1 | 8/2005 | Selmon et al. |
| 2005/0177105 A1 | 8/2005 | Shalev |
| 2005/0216044 A1 | 9/2005 | Hong |
| 2005/0261663 A1 | 11/2005 | Patterson et al. |
| 2006/0094930 A1 | 5/2006 | Sparks et al. |
| 2006/0135984 A1 | 6/2006 | Kramer et al. |
| 2006/0271078 A1 | 11/2006 | Modesitt |
| 2007/0083220 A1 | 4/2007 | Shamay |
| 2007/0088230 A1 | 4/2007 | Terashi et al. |
| 2007/0093779 A1 | 4/2007 | Kugler et al. |
| 2007/0093780 A1 | 4/2007 | Kugler et al. |
| 2007/0093781 A1 | 4/2007 | Kugler et al. |
| 2007/0093782 A1 | 4/2007 | Kugler et al. |
| 2007/0093783 A1 | 4/2007 | Kugler et al. |
| 2007/0265596 A1 | 11/2007 | Jen et al. |
| 2008/0103443 A1 | 5/2008 | Kabrick et al. |
| 2008/0228171 A1 | 9/2008 | Kugler et al. |
| 2008/0243065 A1 | 10/2008 | Rottenberg et al. |
| 2008/0243067 A1 | 10/2008 | Rottenberg et al. |
| 2009/0088685 A1 | 4/2009 | Kugler et al. |
| 2009/0124899 A1 | 5/2009 | Jacobs et al. |
| 2009/0209910 A1 | 8/2009 | Kugler et al. |
| 2009/0270890 A1 | 10/2009 | Robinson et al. |
| 2010/0063534 A1 | 3/2010 | Kugler et al. |
| 2010/0069945 A1 | 3/2010 | Olson et al. |

FOREIGN PATENT DOCUMENTS

| | | |
|---|---|---|
| WO | WO 2008/063621 A2 | 5/2008 |
| WO | WO 2009/054943 A1 | 4/2009 |
| WO | WO 2009/100129 A2 | 8/2009 |
| WO | WO 2009/134346 A2 | 11/2009 |
| WO | WO 2010/019241 A1 | 2/2010 |
| WO | WO 2010/044816 A1 | 4/2010 |

OTHER PUBLICATIONS

Colombo, Antonio et al., *Treating Chronic Total Occlusions Using Subintimal Tracking and Reentry: The STAR Technique,* Catheterization and Cardiovascular Interventions; vol. 64:407-411 (2005).

International Search Report in PCT/US06/35244 dated Mar. 24, 2008.

Written Opinion of International Searching Authority in PCT/US06/35244 dated Mar. 24, 2008.

International Preliminary Report on Patentability in PCT/US06/35244 dated Mar. 17, 2009.

* cited by examiner

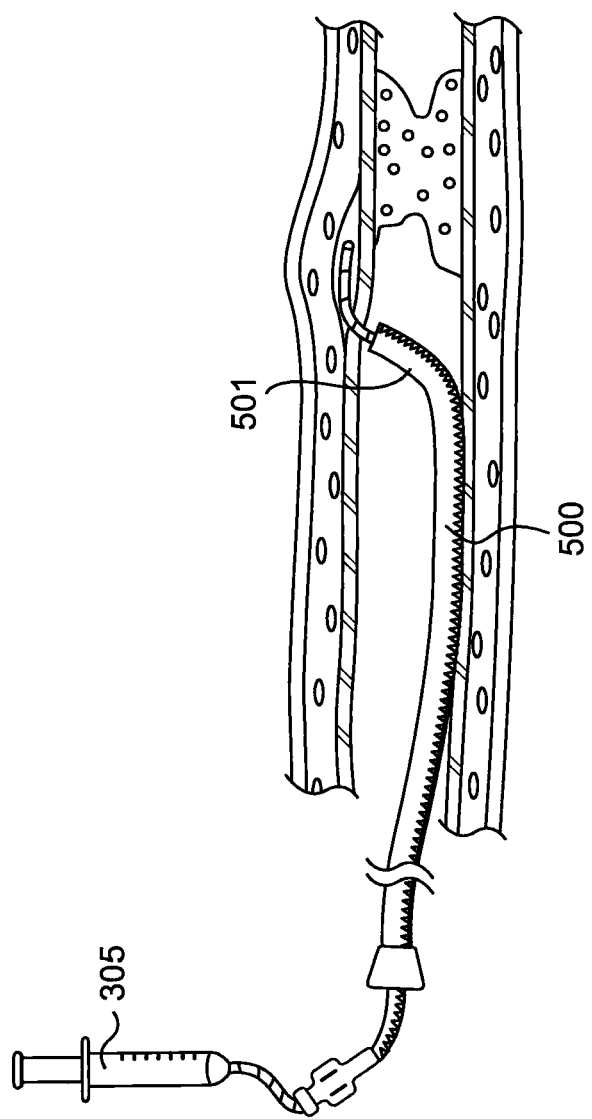

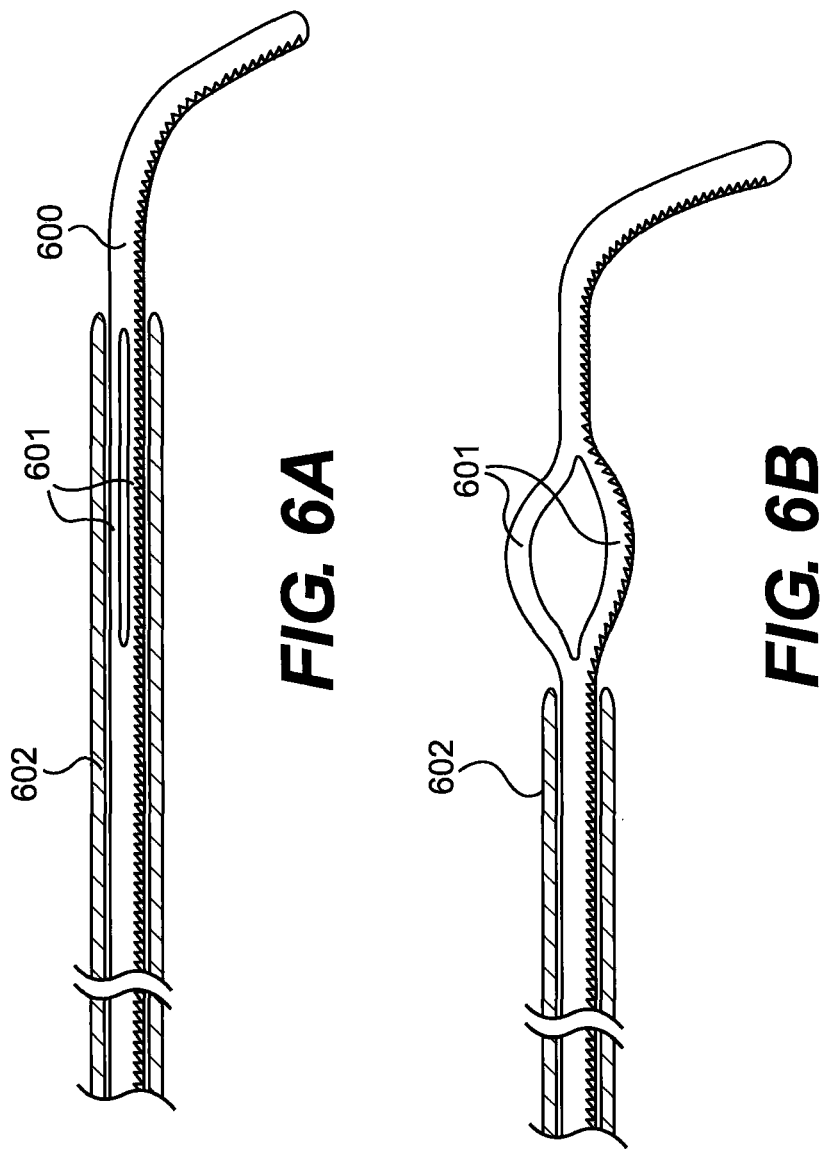

ENDOVASCULAR DEVICES AND METHODS

CROSS REFERENCE TO RELATED APPLICATIONS

This is a continuation of application Ser. No. 11/518,431, filed Sep. 11, 2006, now U.S. Pat. No. 8,025,655 which claims the benefit of U.S. Provisional Application No. 60/716,287, filed Sep. 12, 2005 and U.S. Provisional Application No. 60/717,726, filed Sep. 15, 2005, all of which are incorporated herein by reference.

FIELD OF THE INVENTION

The inventions described herein relate to devices and associated methods for the treatment of chronic total occlusions. More particularly, the inventions described herein relate to devices and methods for crossing chronic total occlusions and subsequently performing balloon angioplasty, stenting, atherectomy, or other endovascular methods for opening occluded blood vessels.

BACKGROUND OF THE INVENTION

Due to age, high cholesterol and other contributing factors, a large percentage of the population has arterial atherosclerosis that totally occludes portions of the patient's vasculature and presents significant risks to patient health. For example, in the case of a total occlusion of a coronary artery, the result may be painful angina, loss of cardiac tissue or patient death. In another example, complete occlusion of the femoral and/or popliteal arteries in the leg may result in limb threatening ischemia and limb amputation.

Commonly known endovascular devices and techniques are either inefficient (time consuming procedure), have a high risk of perforating a vessel (poor safety) or fail to cross the occlusion (poor efficacy). Physicians currently have difficulty visualizing the native vessel lumen, can not accurately direct endovascular devices toward visualized lumen, or fail to advance devices through the lesion. Bypass surgery is often the preferred treatment for patients with chronic total occlusions, but less invasive techniques would be preferred.

SUMMARY OF THE INVENTION

To address this and other unmet needs, the present invention provides, in exemplary non-limiting embodiments, devices and methods for the treatment of chronic total occlusions. The disclosed methods and devices are particularly beneficial in crossing coronary total occlusions but may also be useful in other vessels including peripheral arteries and veins. In exemplary embodiments, total occlusions are crossed using methods and devices intended to provide a physician the ability to place a device within the subintimal space, delaminate the connective tissues between layers within the lesion or vessel wall, or remove tissues from the chronic total occlusion or surrounding vessel.

In an aspect of the disclosure, a subintimal device may be used to guide conventional devices (for example guide wires, stents, lasers, ultrasonic energy, mechanical dissection, or atherectomy) within the vessel lumen. Additionally, a subintimal device may be used to delaminate vessel wall layers and also may be used to remove tissue from the occlusive lesion or surrounding vessel wall. In one example, the positioning of a subintimal device or the establishment of a delamination plane between intima and medial layers is achieved through the use of a mechanical device that has the ability to infuse a fluid (for example saline). Fluid infusion may serve to apply a hydraulic pressure to the tissues and aid in layer delamination and may also serve to protect the vessel wall from the tip of the subintimal device and reduce the chance of vessel perforation. The infusion of fluid may be controlled by pressure or by volume.

Subintimal device placement may be achieved with a subintimal device directing catheter. The catheter may orient a subintimal device so that it passes along the natural delamination plane between intima and media. The catheter may orient the subintimal device in various geometries with respect to the vessel. For example, the subintimal device may be directed substantially parallel with respect to the vessel lumen or in a helical pattern such that the subintimal device encircles the vessel lumen in a coaxial fashion. The subintimal device directing catheter may be an inflatable balloon catheter having proximal and distal ends with two wire lumens. One lumen may accept a conventional guide wire while the second lumen may accept the subintimal device. In an alternative embodiment, the wire directing catheter may be a guide catheter with distal geometry that steers the subintimal device with the appropriate orientation to enter the subintimal space.

In an additional disclosure, a subintimal device intended to mechanically delaminate tissue layers may use a device that is inserted into the subintimal space in a first collapsed configuration and is released or actuated into a second expanded configuration. The device may then be withdrawn or manipulated to propagate the area of delamination.

An additional aspect of the disclosure may allow the physician to remove tissues from the lesion or vessel wall. In one embodiment, a subintimal device is circumferentially collapsed around the total occlusion. Tissue removal is performed through simple device withdrawal or through a procedure that first cuts connective tissues (i.e. the intimal layer proximal and distal of the lesion) and then removes the targeted tissue. In another embodiment, a tissue removal device is passed through the lesion within the native vessel lumen. The targeted tissues may be mechanically engaged and removed through device withdrawal.

BRIEF DESCRIPTION OF THE DRAWINGS

It is to be understood that both the foregoing summary and the following detailed description are exemplary. Together with the following detailed description, the drawings illustrate exemplary embodiments and serve to explain certain principles. In the drawings.

FIG. 5 is a partial sectional view of an additional subintimal device directing guiding catheter embodiment with fluid infusion through the subintimal device;

FIGS. 6A and B are partial sectional views of a expandable delamination catheter;

DETAILED DESCRIPTION OF EXEMPLARY EMBODIMENTS

The following detailed description should be read with reference to the drawings in which similar elements in different drawings are numbered the same. The drawings, which are not necessarily to scale, depict illustrative embodiments and are not intended to limit the scope of the invention.

Figure 1:
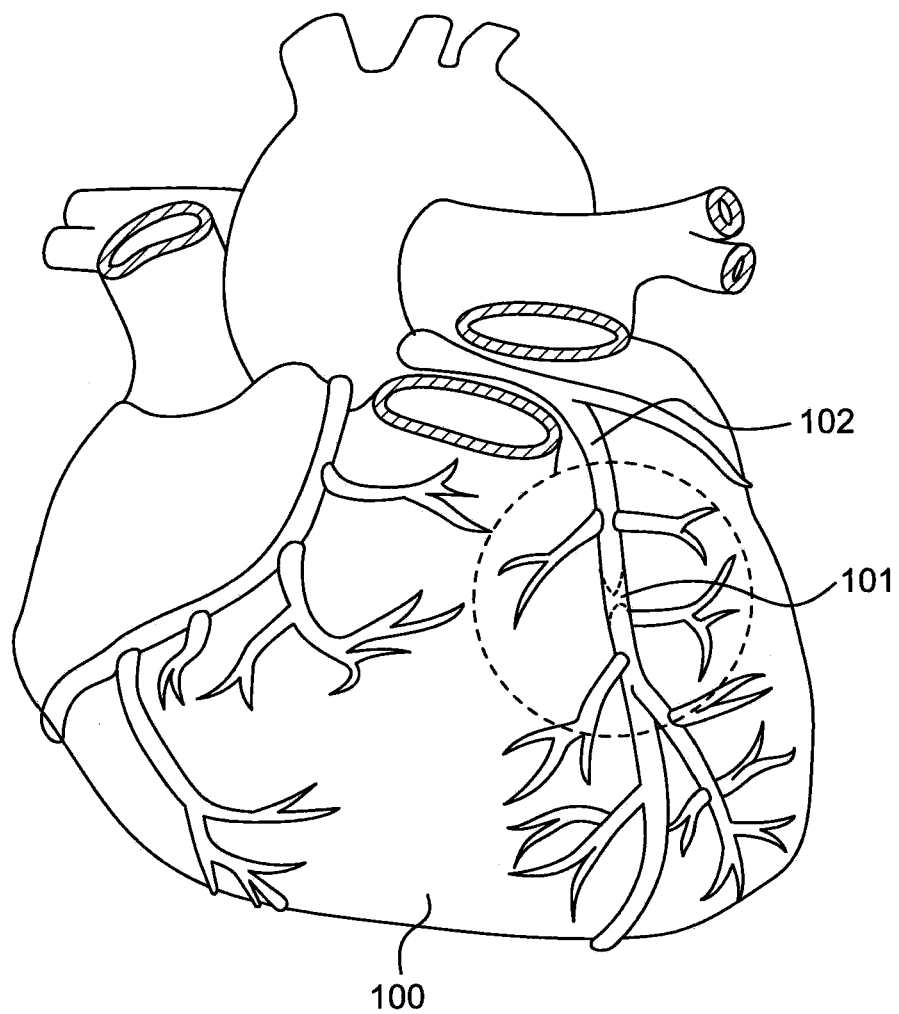
FIG. 1 shows an illustration of a heart showing a coronary artery that contains a chronic total occlusion.
Figure 2:
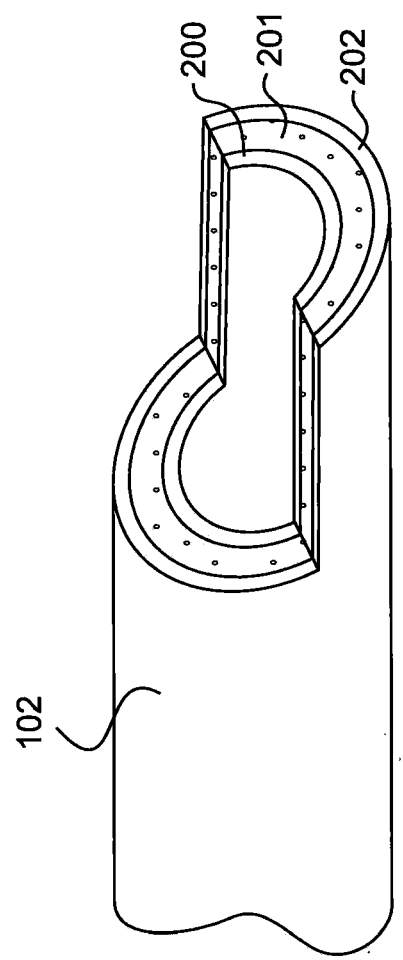
FIG. 2 is a schematic representation of a coronary artery showing the intimal, medial and adventitial layers.

Referring to FIG. 1, a diseased heart 100 includes a chronic total occlusion 101 of a coronary artery 102. FIG. 2 shows coronary artery 102 with intimal layer 200 (for sake of clarity, the multi layer intima is shown as a single homogenous layer). Concentrically outward of the intima is the medial layer 201 (which also is comprised of more than one layer but is shown as a single layer). The transition between the external most portion of the intima and the internal most portion of the media is referred to as the subintimal space. The outermost layer of the artery is the adventitia 202.

Figure 3:
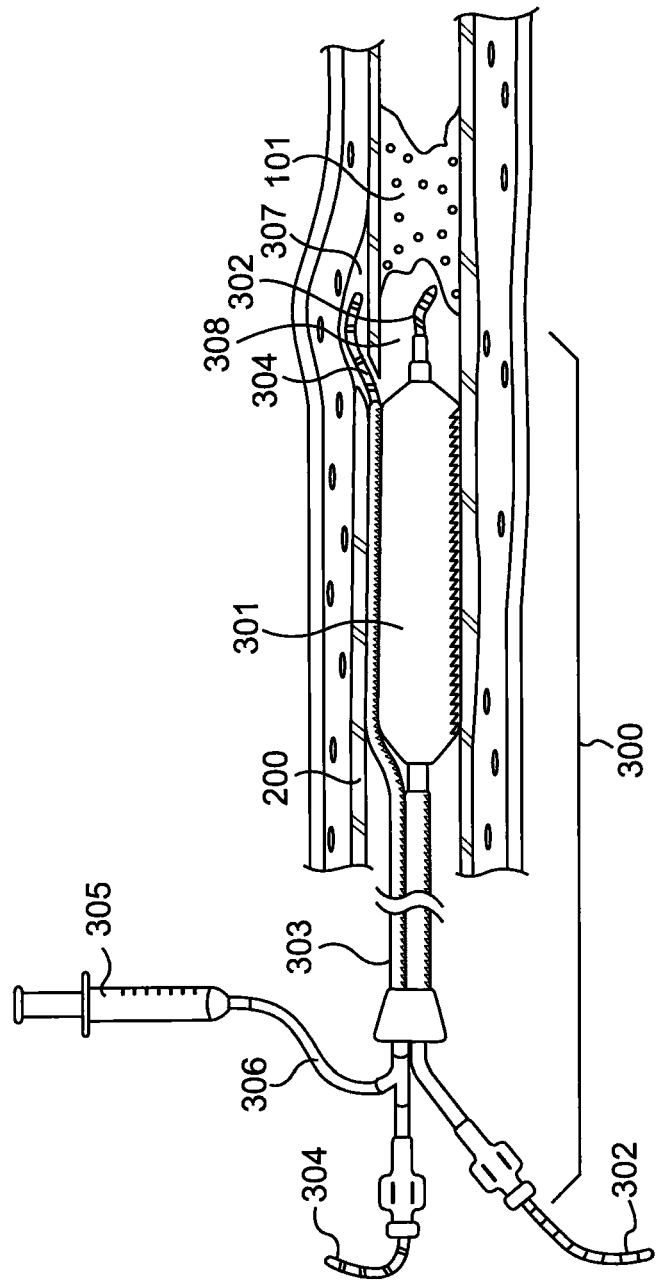
FIG. 3 is a partial sectional view of a subintimal device directing balloon catheter embodiment with fluid infusion through the subintimal device lumen within the device directing catheter.
Figure 4:
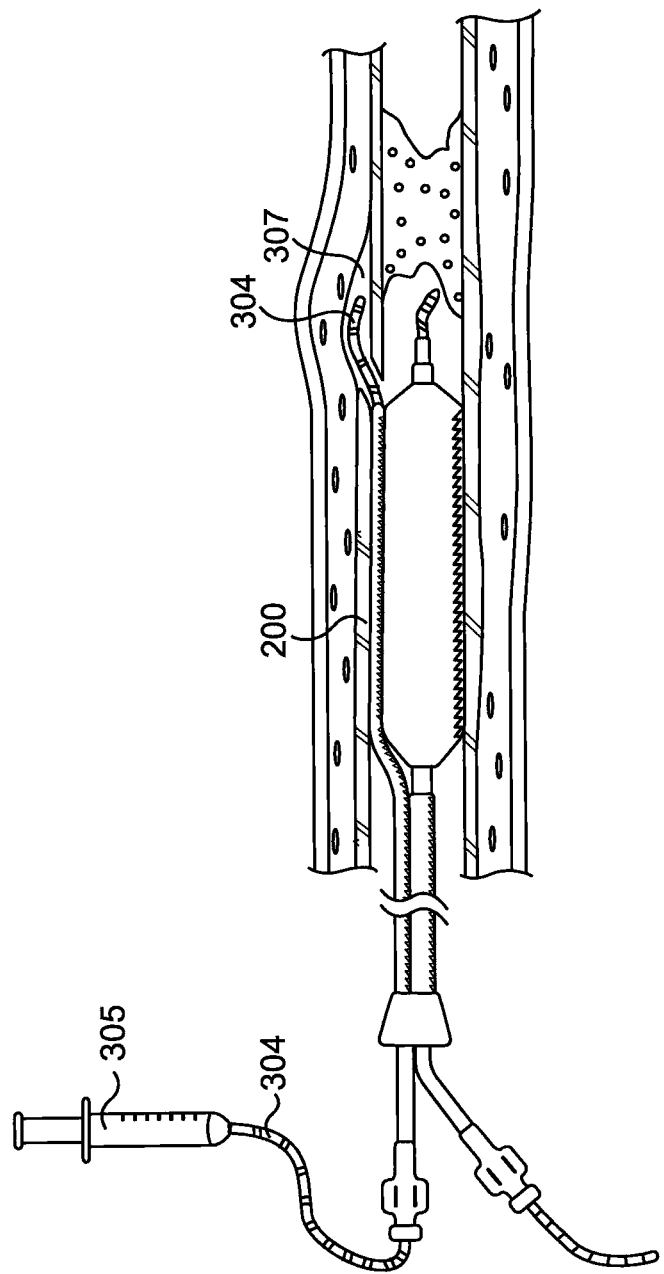
FIG. 4 is a partial sectional view of a subintimal device directing balloon catheter embodiment with fluid infusion through the subintimal device.

In an aspect of the disclosure, a subintimal device may be used to guide conventional devices (for example guide wires, stents, lasers, ultrasonic energy, mechanical dissection, or atherectomy) within the vessel lumen. Additionally, a subintimal device may be used to delaminate vessel wall layers and also may be used to remove tissue from the occlusive lesion or surrounding vessel wall. In one embodiment, FIG. 3 shows a subintimal device directing catheter is 300 with its distal balloon 301 that has been advanced over a conventional guide wire 302 and inflated proximal to chronic total occlusion 101. For the sake of clarity, FIG. 3 shows a subintimal device path that is substantially parallel to the vessel lumen, but other orientations (i.e. helical) may also be considered. Subintimal device lumen 303 is positioned adjacent to the intimal layer 200 and subintimal device 304 has been advanced as to perforate the subintimal layer. A fluid source (i.e. syringe) 305 is in fluid communication with subintimal device lumen 303 through infusion lumen 306. Fluid may flow from the fluid source 305 through the subintimal device lumen 303 under a controlled pressure or a controlled volume. Injecting fluid out of the outlet of the subintimal device lumen and into the vascular wall may create a subintimal space defined by the vascular wall. The infused fluid may enter the subintimal space 307 directly from the subintimal device lumen 303 or from the volume 308 defined by the distal end of the balloon 301 and the proximal edge of the lesion 101. FIG. 4 shows an alternative fluid infusion path where fluid source 305 is in fluid communication with a lumen within the subintimal device 304. FIG. 5 shows an alternative subintimal device directing guide catheter 500 where the distal end 501 has a predefined shape or the distal end has an actuating element that allows manipulation by the physician intra-operatively.

Another aspect of the disclosure may place a subintimal device within the subintimal space in a first collapsed configuration and releases or actuates the subintimal device to a second expanded configuration. The device may then be withdrawn or manipulated to propagate the subintimal dissection. In one embodiment, FIG. 6A shows a subintimal device with internal expandable element 600 that contains one or more expanding elements 601 contained in exterior sheath 602. FIG. 6B shows exterior sheath 602 in a retracted position allowing expanding elements 601 to elastically expand. The subintimal device is intended to be delivered through the aforementioned subintimal device delivery catheters.

Figure 7A:
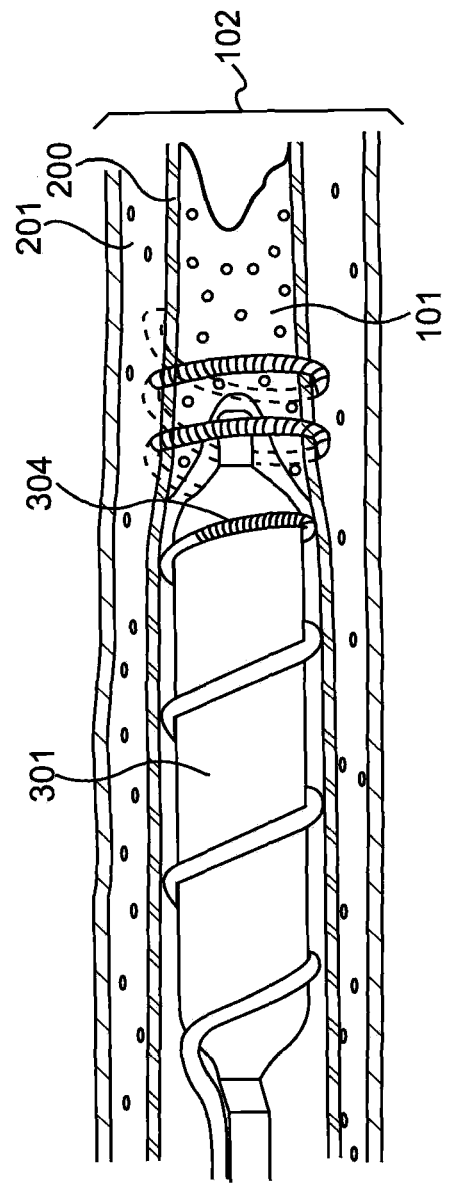
FIGS. 7 A-D are partial sectional views of a circumferential subintimal tissue removal device.
Figure 7B:
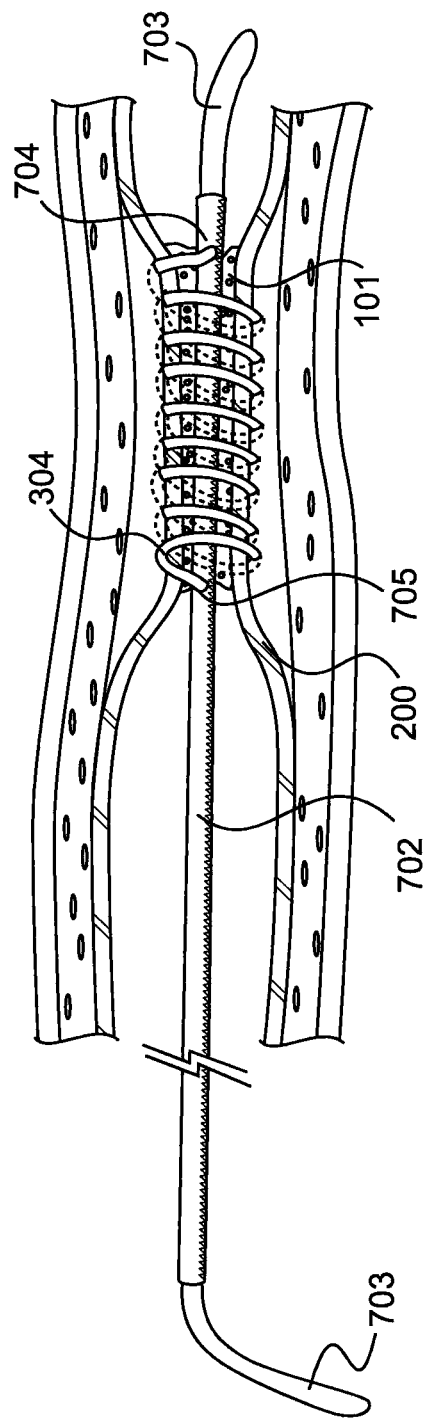
Figure 7C:
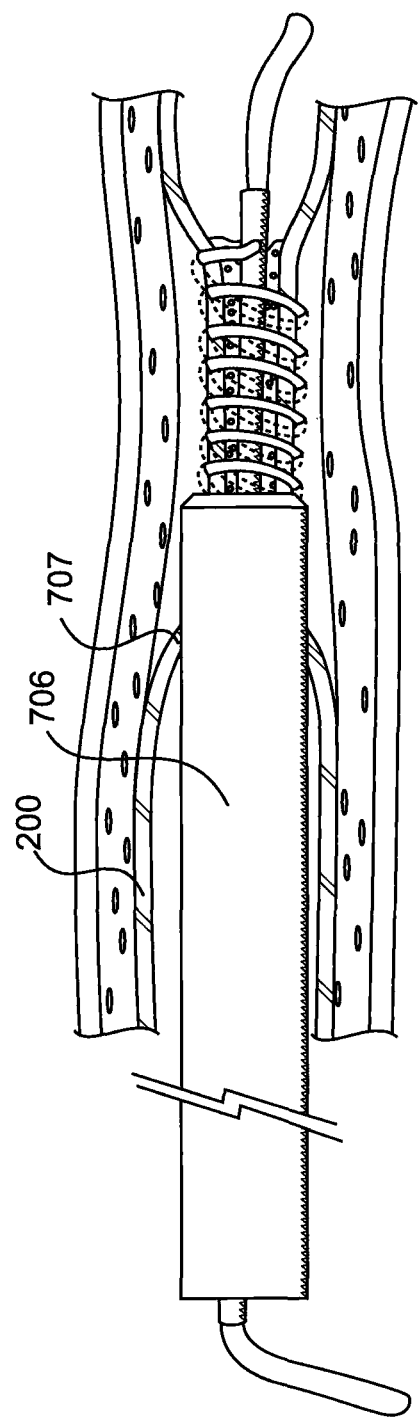
Figure 7D:
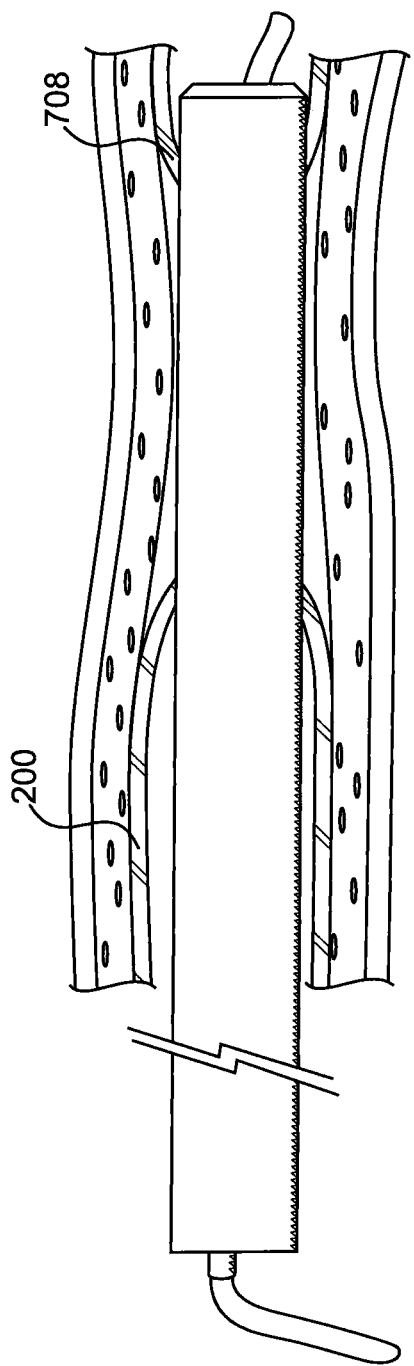

An additional aspect of the disclosure may allow the physician to remove tissues from the lesion or vessel wall. FIG. 7A shows an embodiment where subintimal device directing balloon catheter is inflated within coronary artery 102 just proximal to chronic total occlusion 101. Subintimal device 304 is partially delivered around chronic total occlusion 102 coaxially outside the intimal layer 200 and coaxially inside medial layer 201 in a helical pattern. FIG. 7B shows a subintimal device capture catheter 702 positioned across the chronic total occlusion 101 over conventional guide wire 703 and within subintimal device 304. The distal 704 and proximal 705 ends of the subintimal device 304 have been captured and rotated as to reduce the subintimal device outside diameter and contain the lesion 101 and intima 200 within the coils' internal diameter. The device may be withdrawn through the use of a cutting element. For example, FIGS. 7C and D show the advancement of a cutting element 706 in two stages of advancement showing the cutting of intima 200 proximal of the occlusion 707 and intimal distal of the occlusion 708.

Figure 8A:
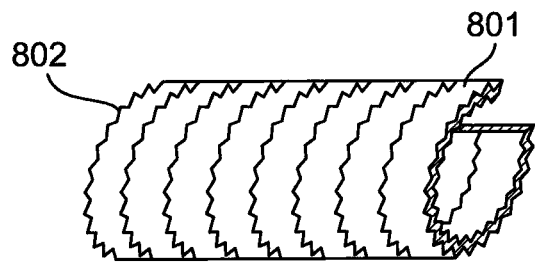
FIGS. 8A-C are an example of subintimal device construction.
Figure 8B:
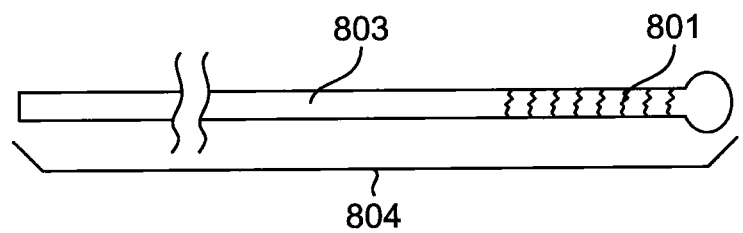
Figure 8C:
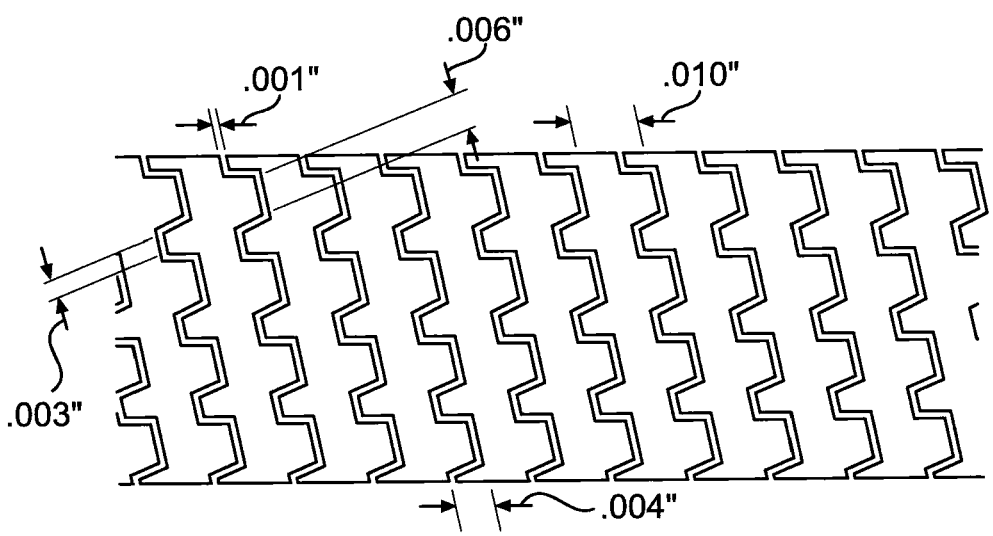

An additional aspect of the subintimal device is the construction of the device body. The flexibility and torquability of the device body can affect the physician's ability to achieve a subintimal path. The subintimal device body may be constructed in part or in to total of a single layer coil with geometric features along the coil length that allow adjacent coils to engage (for example mechanical engagement similar to the teeth of a gear). FIG. 8A shows coil 801 closely wound such that the multitude of teeth 802 along the coil edges are in contact such that the peaks of one coil falls within the valleys of the adjacent coil. A conventional coil reacts to an applied torsional load by diametrically expanding or contracting, thus forcing the wire surfaces within a turn of the coil to translate with respect to its neighboring turn. The construction of coil 801 resists the translation of wire surfaces within the coil thus resisting the diametric expansion or contraction (coil deformation). An increased resistance to coil deformation increases the torsional resistance of the device body while the coiled construction provides axial flexibility. An exemplary construction may include a metallic tube where the coil pattern 801 and teeth 802 are cut from the tube diameter using a laser beam. FIG. 8B shows subintimal device body 804 that is for example a continuous metallic tube with distal laser cut coil segment 801 and proximal solid tube 803. Tube materials include but are not limited to stainless steel and nickel titanium. Alternatively, the coil may be wound from a continuous wire. The wire has a cross section that for example has been mechanically deformed (stamped) to form the teeth and allow coil engagement. FIG. 8C shows an example of a laser cut tooth pattern from the circumference of a tube that has been shown in a flat configuration for purposes of illustration.

Figure 9A:
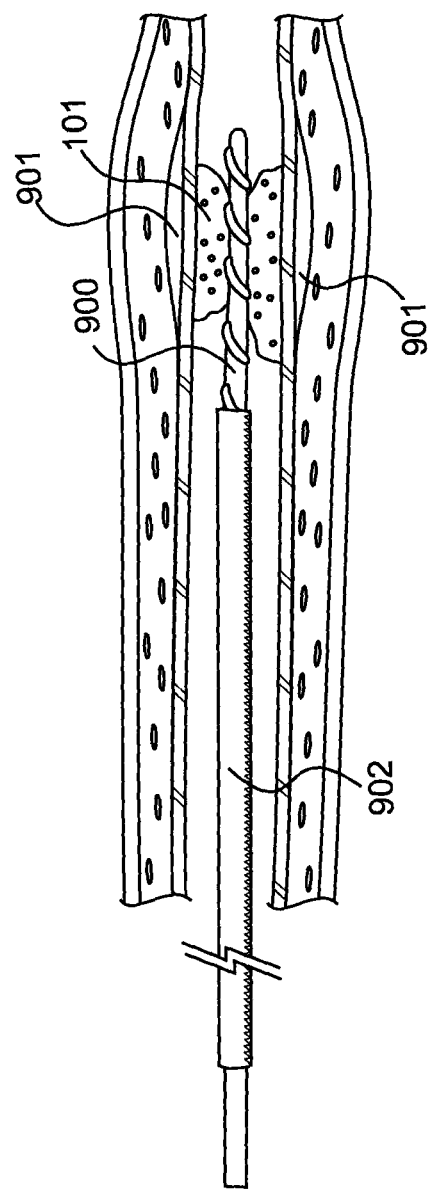
FIGS. 9A and B are partial sectional views of an intraluminal rotational engagement tissue removal device.
Figure 9B:
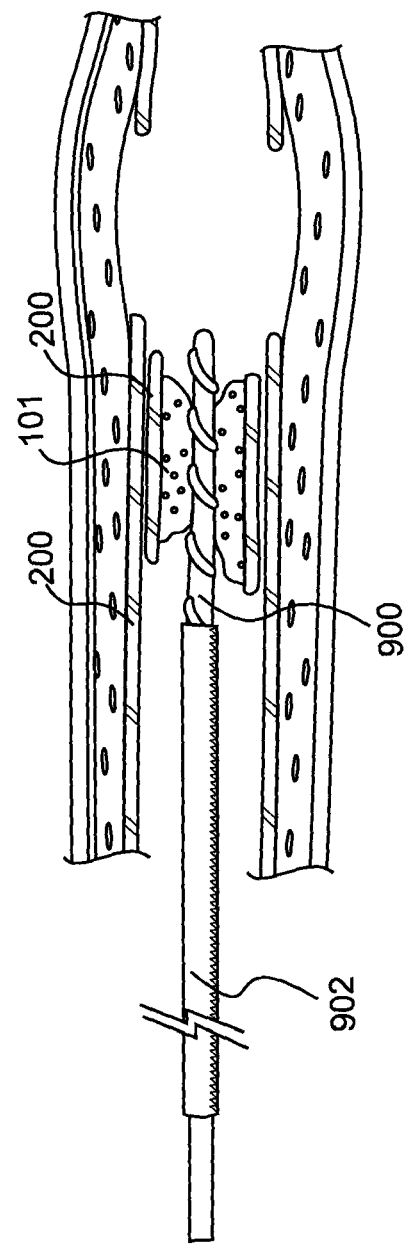

In another embodiment, a tissue removal device may be passed through the lesion within the native vessel lumen. FIG. 9A shows corkscrew device 900 with exterior sheath 902 engaging occlusion after delamination of the intimal layer 901 has been performed by the aforementioned methods and devices. FIG. 9B shows removal of the occlusion and a portion of the intimal layer through axial withdrawal of the corkscrew device.

From the foregoing, it will be apparent to those skilled in the art that the present invention provides, in exemplary non-limiting embodiments, devices and methods for the treatment of chronic total occlusions. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of treating a vascular wall defining a vascular lumen, the vascular wall comprising an intima and an adventitia, the method including:
    inserting a catheter into the vascular lumen, the catheter including a first tubular member defining a first lumen, an inflatable member located about the first tubular member; and a second tubular member defining a second lumen having an outlet, the second tubular member adjacent an outer surface of the inflatable member;
    inflating the inflatable member to move the second tubular member radially away from a central axis of the first tubular member; and
    injecting fluid out of the outlet of the second lumen and into the vascular wall creates a subintimal space defined by the vascular wall.

2. The method of claim 1, wherein the injection of fluid delaminates tissue layers in a subintimal space defined by the vascular wall.

3. The method of claim 1, further including inserting a subintimal device into a subintimal space defined by the blood vessel wall via the second lumen of the second tubular member.

4. The method of claim 1, wherein the fluid is injected between the intima and the adventitia of the vascular wall.

* * * * *